US012746007B2

(12) United States Patent
Anderson et al.

(10) Patent No.: US 12,746,007 B2
(45) Date of Patent: Sep. 29, 2026

(54) IMPLANTABLE MEDICAL DEVICE WITH SEALING TO ACCOMMODATE AN IRREGULAR OSTIUM

(71) Applicant: BOSTON SCIENTIFIC SCIMED, INC., Maple Grove, MN (US)

(72) Inventors: James M. Anderson, Corcoran, MN (US); Jerry Wang, Edina, MN (US); Joshua Mark Inouye, Brooklyn Park, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 205 days.

(21) Appl. No.: 18/494,244

(22) Filed: Oct. 25, 2023

(65) Prior Publication Data

US 2024/0138844 A1 May 2, 2024

Related U.S. Application Data

(60) Provisional application No. 63/419,403, filed on Oct. 26, 2022.

(51) Int. Cl.

*A61B 17/12* (2006.01)
*A61B 17/00* (2006.01)
*A61F 2/01* (2006.01)

(52) U.S. Cl.

CPC .. *A61B 17/12122* (2013.01); *A61B 17/12172* (2013.01); *A61B 17/12177* (2013.01);

(Continued)

(58) Field of Classification Search

CPC ........ A61B 17/12109; A61B 17/12031; A61B 17/121113; A61B 17/12122;

(Continued)

(56) References Cited

U.S. PATENT DOCUMENTS

| | | | | |
|---|---|---|---|---|
| 2001/0018095 A1* | 8/2001 | Shlenker | A61L 31/14 | 427/407.1 |
| 2014/0100597 A1* | 4/2014 | Wang | A61F 2/012 | 606/200 |

(Continued)

FOREIGN PATENT DOCUMENTS

CN 215821043 U 2/2022

OTHER PUBLICATIONS

International Search Report and Written Opinion for International Application No. PCT/US2023/077745, dated Feb. 19, 2024.

*Primary Examiner* — Elizabeth Houston
*Assistant Examiner* — Lindsey Bachman
(74) *Attorney, Agent, or Firm* — Seager, Tufte & Wickhem LLP

(57) ABSTRACT

An implantable medical device includes an expandable frame that is expandable between a collapsed configuration for delivery and an expanded configuration for deployment, the expandable frame including a periphery defined by the expandable frame. A covering spans at least part of the expandable frame. An expandable element is secured relative to the periphery, the expandable element is adapted to seal against an irregular body opening such as an irregular-shaped ostium of a patient's LAA (left atrial appendage).

7 Claims, 9 Drawing Sheets

(52) U.S. Cl.
CPC ............ *A61F 2/0105* (2020.05); *A61F 2/012* (2020.05); *A61B 2017/00632* (2013.01); *A61B 2017/00893* (2013.01)

(58) Field of Classification Search
CPC ........ A61B 17/12168; A61B 17/12172; A61B 17/12177; A61B 17/12181; A61F 2/01; A61F 2/012; A61F 2/0105; A61F 2/0108
See application file for complete search history.

(56) References Cited

U.S. PATENT DOCUMENTS

| | | | | |
|---|---|---|---|---|
| 2015/0133989 | A1 | 5/2015 | Lubock et al. | |
| 2016/0331382 | A1 | 11/2016 | Center et al. | |
| 2018/0206851 | A1 | 7/2018 | Walzman | |
| 2019/0083075 | A1* | 3/2019 | Onushko .......... | A61B 17/12122 |
| 2020/0178981 | A1 | 6/2020 | Anderson et al. | |
| 2020/0253615 | A1 | 8/2020 | Melanson et al. | |
| 2020/0261219 | A1 | 8/2020 | Kumar et al. | |
| 2021/0068842 | A1 | 3/2021 | Griffin | |

* cited by examiner

IMPLANTABLE MEDICAL DEVICE WITH SEALING TO ACCOMMODATE AN IRREGULAR OSTIUM

CROSS REFERENCE TO RELATED APPLICATIONS

This application claims the benefit of priority of U.S. Provisional Application No. 63/419,403 filed Oct. 26, 2022, the entire disclosure of which is hereby incorporated by reference.

TECHNICAL FIELD

The disclosure relates generally to medical devices and more particularly to medical devices that are adapted for use in percutaneous medical procedures including implantation into the left atrial appendage (LAA) of a heart.

BACKGROUND

The left atrial appendage is a small organ attached to the left atrium of the heart. During normal heart function, as the left atrium constricts and forces blood into the left ventricle, the left atrial appendage constricts and forces blood into the left atrium. The ability of the left atrial appendage to contract assists with improved filling of the left ventricle, thereby playing a role in maintaining cardiac output. However, in patients suffering from atrial fibrillation, the left atrial appendage may not properly contract or empty, causing stagnant blood to pool within its interior, which can lead to the undesirable formation of thrombi within the left atrial appendage.

Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation originate in the left atrial appendage. As a treatment, medical devices have been developed which are deployed to close off the left atrial appendage. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices. An example may be found in an implantable medical device. The implantable medical device includes an expandable frame expandable between a collapsed configuration for delivery and an expanded configuration for deployment, the expandable frame including a periphery defined by the expandable frame. A covering spans at least part of the expandable frame. An expandable element is secured relative to the periphery and is adapted to seal against an irregular body opening.

Alternatively or additionally, the irregular body opening may include an ostium of a patient's LAA (left atrial appendage).

Alternatively or additionally, the expandable element may include a plurality of bag filters that are arranged around the periphery.

Alternatively or additionally, each of the plurality of bag filters may have an open end and a closed end, and each of the plurality of bag filters may be arranged around the periphery with the open end facing one direction and the closed end facing an opposing direction.

Alternatively or additionally, each of the plurality of bag filters may have an open end and a closed end, and each of the plurality of bag filters may be arranged around the periphery in an alternating matter, with the open end of a bag filter arranged proximate a closed end of a neighboring bag filter.

Alternatively or additionally, at least some of the plurality of bag filters may have two open ends, with a one-way valve that limits blood flow therethrough.

Alternatively or additionally, at least some of the plurality of bag filters may include a coagulant disposed within the bag filters.

Alternatively or additionally, the expandable element may include a corrugated tri-layer element extending around the periphery, the corrugated tri-layer element including an inner layer, an outer layer and an intervening middle layer that alternates between attachment to the inner layer and attachment to the outer layer.

Alternatively or additionally, the corrugated tri-layer element may include a coagulant.

Alternatively or additionally, the expandable element may include an omni-directional valved mesh.

Alternatively or additionally, the implantable medical device may include an LAAC (left atrial appendage closure) device.

Another example may be found in an LAAC (left atrial appendage closure) device adapted to fit within an irregular ostium of a patient's LAA (left atrial appendage). The LAAC device includes an expandable frame expandable between a collapsed configuration for delivery and an expanded configuration for deployment, the expandable frame including a periphery defined by the expandable frame. A covering spans at least part of the expandable frame. An expandable element is adapted to seal against an irregular ostium of the patient's LAA.

Alternatively or additionally, the expandable element may include a coagulant.

Alternatively or additionally, the expandable element may include a swellable member.

Alternatively or additionally, the expandable element may include a plurality of bag filters.

Another example may be found in an LAAC (left atrial appendage closure) device adapted to fit within an irregular ostium of a patient's LAA (left atrial appendage). The LAAC device includes an expandable frame expandable between a collapsed configuration for delivery and an expanded configuration for deployment, the expandable frame including a periphery defined by the expandable frame. A covering spans at least part of the expandable frame. A plurality of bag filters are arranged around the periphery.

Alternatively or additionally, each of the plurality of bag filters may have an open end and a closed end, and each of the plurality of bag filters may be arranged around the periphery with the open end facing one direction and the closed end facing an opposing direction.

Alternatively or additionally, each of the plurality of bag filters may have an open end and a closed end, and each of the plurality of bag filters may be arranged around the periphery in an alternating matter, with the open end of a bag filter arranged proximate a closed end of a neighboring bag filter.

Alternatively or additionally, at least some of the plurality of bag filters may have two open ends, with a one-way valve that limits blood flow therethrough.

Alternatively or additionally, at least some of the plurality of bag filters may include a coagulant disposed within the bag filters.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
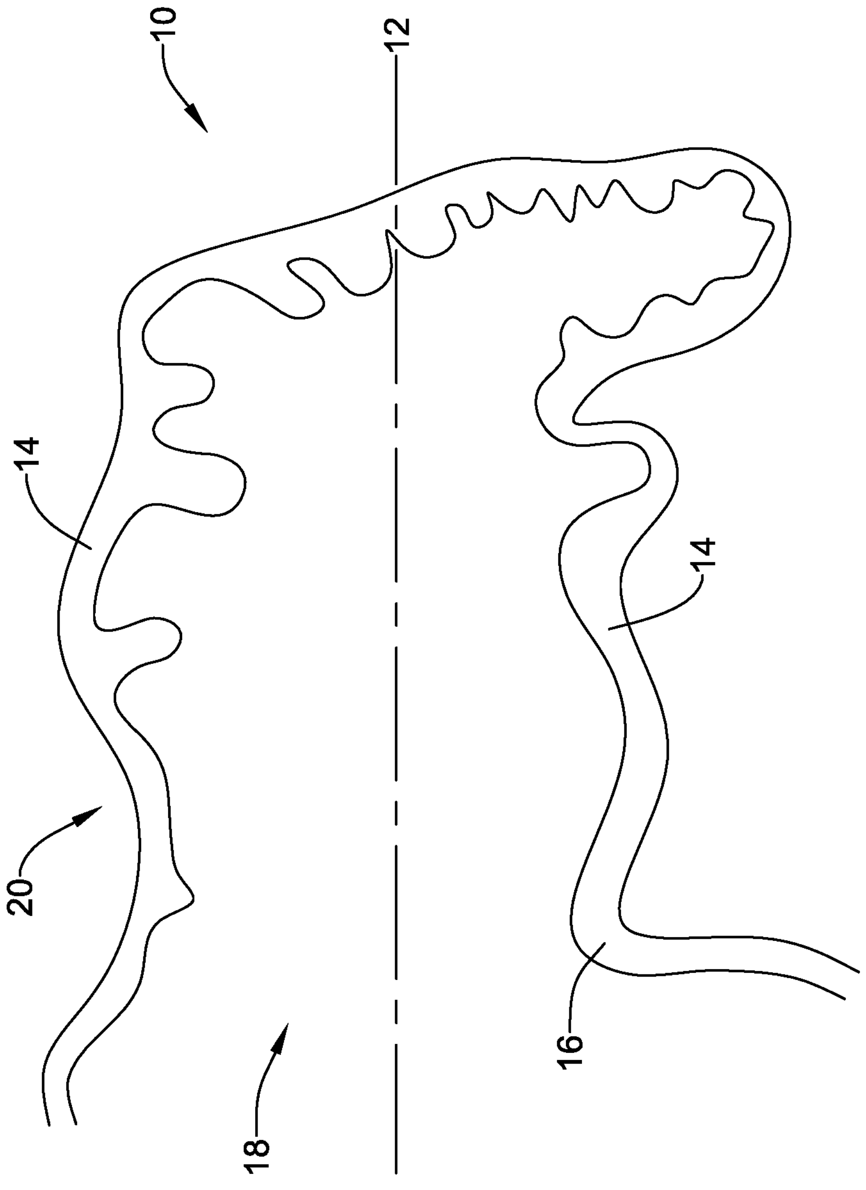
FIG. 1 is a partial cross-sectional view of an LAA (left atrial appendage)

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

The following description should be read with reference to the drawings, which are not necessarily to scale, wherein like reference numerals indicate like elements throughout the several views. The detailed description and drawings are intended to illustrate but not limit the present disclosure. Those skilled in the art will recognize that the various elements described and/or shown may be arranged in various combinations and configurations without departing from the scope of the disclosure. The detailed description and drawings illustrate example embodiments of the disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the present disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean the greatest measurement of a stated or identified dimension, unless the extent or dimension in question is preceded by or identified as a "minimum", which may be understood to mean the smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to use the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The following figures illustrate selected components and/or arrangements of an implant for occluding the left atrial appendage, a system for occluding the left atrial appendage, and/or methods of using the implant and/or the system. It should be noted that in any given figure, some features may not be shown, or may be shown schematically, for simplicity. Additional details regarding some of the components of the implant and/or the system may be illustrated in other figures in greater detail. While discussed in the context of occluding the left atrial appendage, the implant and/or the system may also be used for other interventions and/or percutaneous medical procedures within a patient. Similarly, the devices and methods described herein with respect to percutaneous deployment may be used in other types of surgical procedures, as appropriate. For example, in some examples, the devices may be used in a non-percutaneous procedure. Devices and methods in accordance with the disclosure may also be adapted and configured for other uses within the anatomy.

FIG. 1 is a partial cross-sectional view of a left atrial appendage 10. In some embodiments, the left atrial appendage (LAA) 10 may have a complex geometry and/or irregular surface area. It will be appreciated that the illustrated LAA 10 is merely one of many possible shapes and sizes for the LAA 10, which may vary from patient to patient. Those of skill in the art will also recognize that the medical devices, systems, and/or methods disclosed herein may be adapted for various sizes and shapes of the LAA 10, as necessary. The left atrial appendage 10 may include a generally longitudinal axis 12 arranged along a depth of a main body 20 of the left atrial appendage 10. The main body 20 may include a lateral wall 14 and an ostium 16 forming a proximal mouth 18. In some examples, a lateral extent of the ostium 16 and/or the lateral wall 14 may be smaller or less than a depth of the main body 20 along the longitudinal axis 12, or a depth of the main body 20 may be greater than a lateral extent of the ostium 16 and/or the lateral wall 14. In some examples, the LAA 10 may narrow quickly along the depth of the main body 20 or the left atrial appendage may maintain a generally constant lateral extent along a majority of depth of the main body 20. In some examples, the LAA 10 may include a distalmost region formed or arranged as a tail-like element associated with a distal portion of the main body 20. In some examples, the distalmost region may protrude radially or laterally away from the longitudinal axis 12.

Figure 2:
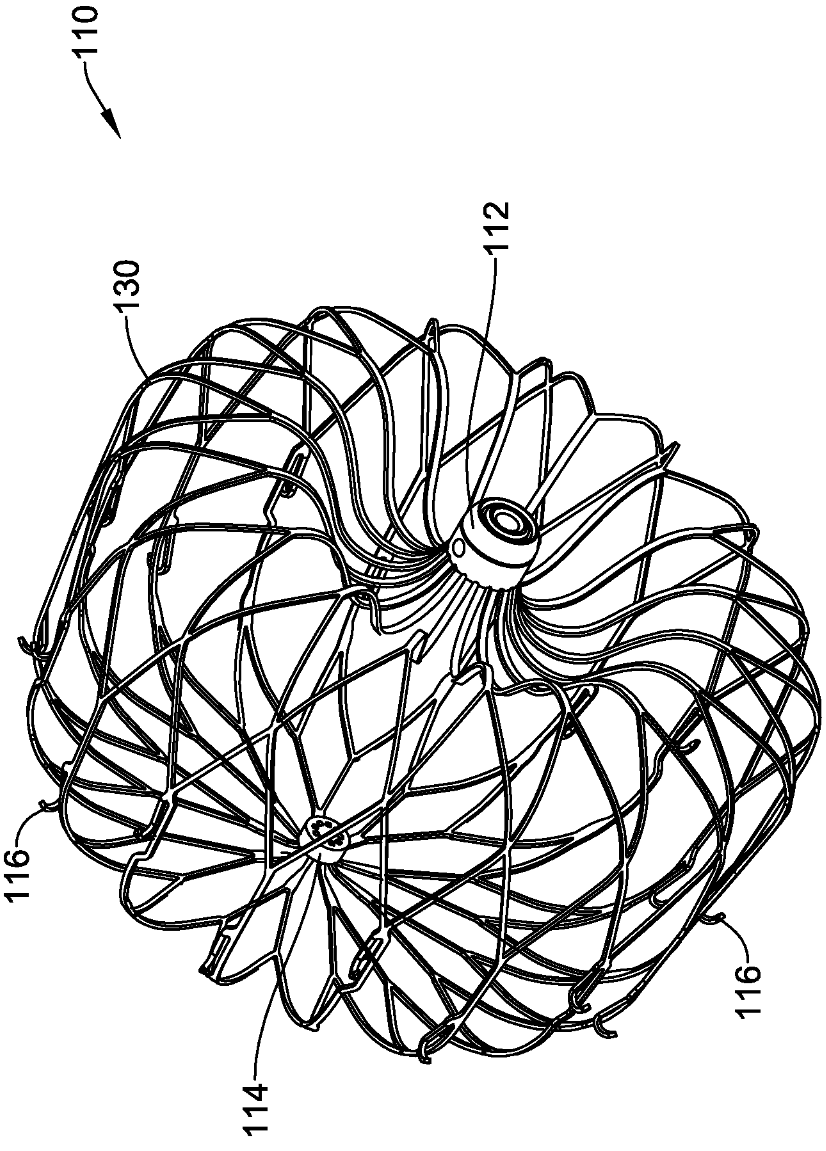
FIG. 2 is a perspective view of an illustrative LAAC (left atrial appendage closure) device, shown without a covering.
Figure 3:
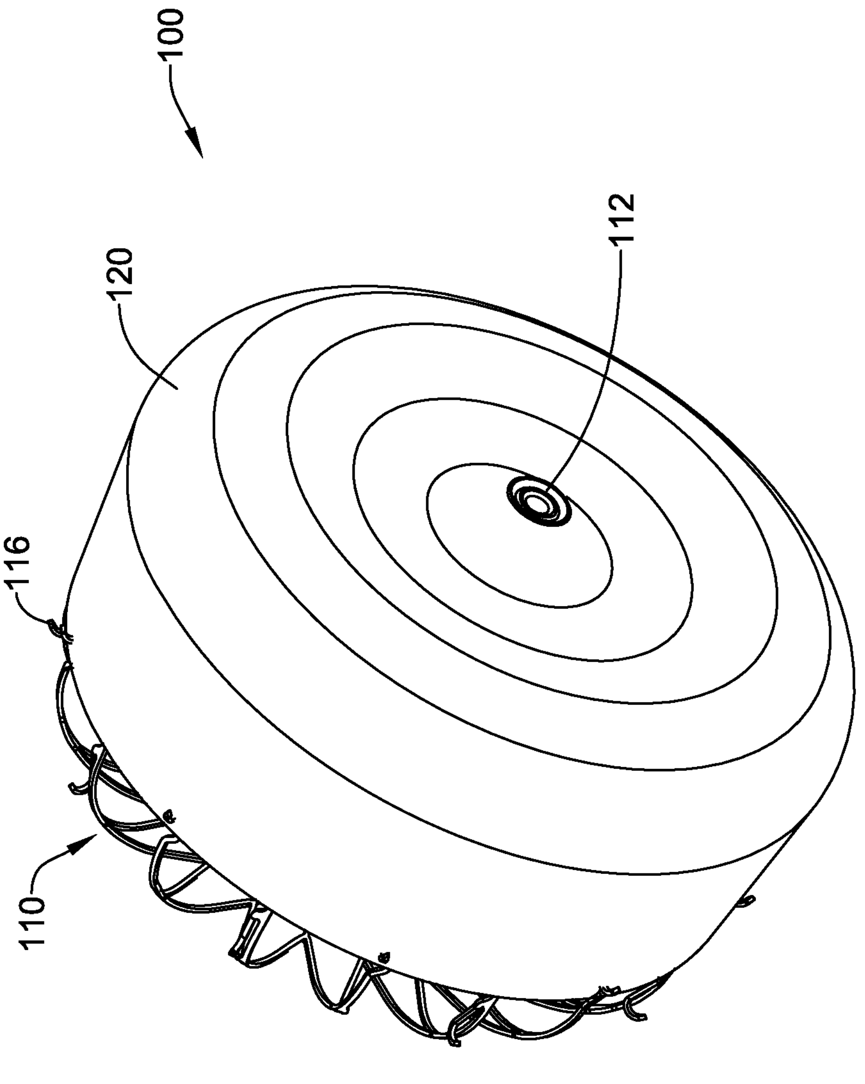
FIG. 3 is a perspective view of the illustrative LAAC device of FIG. 2, including a covering.

In some instances, a device known as an LAAC (left atrial appendage closure) device may be implanted within the LAA 10, such as near or within the ostium 16, in order to seal off the interior of the LAA 10 from the rest of the heart interior. FIGS. 2 and 3 provide views of a left atrial appendage closure (LAAC) device 100. The LAAC device 100 may include an expandable framework 110 configured to shift axially and/or radially along a central longitudinal axis between the fully constrained configuration and the fully unconstrained configuration. In the fully constrained configuration, the expandable framework 110 may be axially elongated and/or radially compressed. In the fully unconstrained configuration, the expandable framework 110 may be axially shortened and/or radially expanded.

As seen in FIG. 3, which illustrates selected features of the LAAC device 100 in the fully unconstrained configuration, the expandable framework 110 may have a plurality of struts disposed about the central longitudinal axis. In some embodiments, the plurality of struts may define a plurality of cells. In some embodiments, the plurality of cells may be a plurality of closed cells. In some embodiments, the plurality of cells may be a plurality of open cells. In some embodiments, the plurality of cells may include a plurality of open cells and a plurality of closed cells in various combinations and/or arrangements.

The expandable framework 110 may include a proximal hub 112 and a distal hub 114. In some embodiments, the proximal hub 112 and/or the distal hub 114 may be centered on and/or coaxial with the longitudinal axis. The plurality of struts may be joined together at and/or fixedly attached to the proximal hub 112 and/or the distal hub 114. The proximal hub 112 may be configured to releasably connect, secure, and/or attach the LAAC device 100 and/or the expandable framework 110 to a delivery device. In some embodiments, the proximal hub 112 may include internal threads configured to rotatably and/or threadably engage an externally threaded distal end of a delivery device. Other configurations for releasably securing the left atrial appendage closure device 100 to a delivery device are also contemplated. As noted herein, some features are not shown in every figure to improve clarity.

The expandable framework 110 and/or the plurality of struts may be formed and/or cut from a tubular member. In some embodiments, the expandable framework 110 and/or the plurality of struts may be integrally formed and/or cut from a unitary member. In some embodiments, the expandable framework 110 and/or the plurality of struts may be integrally formed and/or cut from a unitary tubular member and subsequently formed and/or heat set to a desired shape in the fully unconstrained configuration. In some embodiments, the expandable framework 110 and/or the plurality of struts may be integrally formed and/or cut from a unitary flat member or sheet, and then rolled or formed into a tubular structure and subsequently formed and/or heat set to the desired shape in the fully unconstrained configuration. Some exemplary means and/or methods of making and/or forming the expandable framework 110 and/or the plurality of struts include laser cutting, machining, punching, stamping, electro discharge machining (EDM), chemical dissolution, etc. Other means and/or methods are also contemplated.

In some embodiments, the expandable framework 110 may include at least one anchoring member 116 extending radially outward therefrom in the fully unconstrained configuration. In some embodiments, the expandable framework 110 may include at least one anchoring member 116 extending radially outward from the expandable framework 110. In some embodiments, the expandable framework 110 may include at least one anchoring member 116 extending radially outward from the expandable framework 110 proximate a proximal shoulder of the expandable framework 110. In some embodiments, the expandable framework 110 may include at least one anchoring member 116 extending radially outward from the expandable framework 110 proximate a midsection of the expandable framework 110. In some embodiments, the at least one anchoring member 116 may be configured to engage with the lateral wall of the main body of the left atrial appendage. In some embodiments, the at least one anchoring member 116 may be formed as J-shaped hooks having a free end extending in and/or directed toward a proximal direction with respect to the central longitudinal axis of the left atrial appendage closure device 100 and/or the expandable framework 110. Other configurations are also contemplated.

Figure 4:
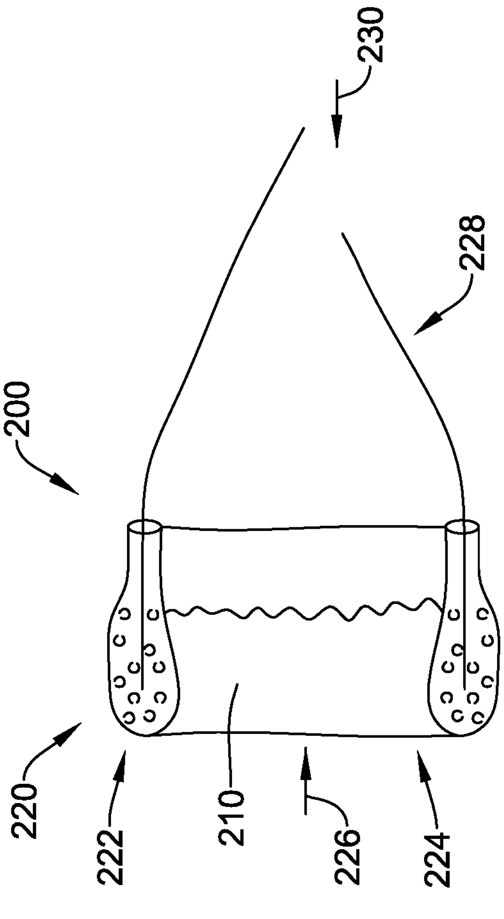
FIG. 4 is a schematic cross-sectional view of an illustrative LAAC device.

In some embodiments, the LAAC device 100 may optionally include the occlusive element 120 connected to, disposed on, disposed over, disposed about, and/or disposed radially outward of at least a portion of the expandable framework 110 and/or the plurality of struts, as seen in FIG. 4. In some embodiments, the occlusive element 120 may be attached to the proximal hub 112 and/or may be attached to the expandable framework at the proximal hub 112. In some embodiments, the occlusive element 120 may extend radially outward from and/or may extend distally from the proximal hub 112. In some embodiments, the occlusive element 120 may be attached and/or secured to the expandable framework 110 at a plurality of discrete locations. In some embodiments, one of, some of, and/or all of the at least one anchoring member 116 may extend through an occlusive element 120, where present.

In some embodiments, the occlusive element 120 may include a membrane, a fabric, a mesh, a tissue element, or another suitable construction. In some embodiments, the occlusive element 120 may be porous. In some embodiments, the occlusive element 120 may be non-porous. In some embodiments, the occlusive element 120 may be permeable to selected gases and/or fluids. In some embodiments, the occlusive element 120 may be substantially impermeable to selected gases and/or fluids, such as blood, water, etc. In some embodiments, the occlusive element 120 may be designed, sized, and/or configured to prevent thrombus and/or embolic material from passing out of the LAA 10 into the left atrium and/or the patient's bloodstream. In some embodiments, the occlusive element 120 may be configured to promote endothelization after implantation, thereby effectively removing the target site (e.g., the left atrial appendage, etc.) from the patient's circulatory system. Some suitable, but non-limiting, examples of materials for the occlusive element 120 are discussed below.

As would be understood by the skilled person, anatomical features may vary in size and/or shape. In some embodiments, the LAA may have an irregular (e.g., elongated and/or oblong) cross-sectional shape. In some embodiments, the expandable framework 110 may be compliant and substantially conform to and/or be in sealing engagement with the shape and/or geometry of a lateral wall of an LAA 10 when deployed and/or expanded therein. In some embodiments, the LAAC device 100 may expand to a size, extent, or shape less than or different from the fully unconstrained configuration, as determined by the surrounding tissue and/or lateral wall of the left atrial appendage. In some embodiments, the expandable framework 110 may be configured to shape and/or stretch the tissue of the LAA such that the lateral wall of the LAA 10 substantially conforms to an outer shape of the expandable framework 110. Other configurations are also contemplated.

In some cases, the LAAC device 100 may be adapted to help with sealing around an irregular shaped ostium 16 of the LAA 10. In some cases, as shown in FIGS. 2 and 3, the LAAC device 100 may be considered as having an overall circular shape. A round shape may not fit well against an ostium such as the ostium 16 that is not round, but rather is oval in shape or perhaps has an irregular border around at least part of the ostium. The following Figures provide illustrative but non-limiting examples of LAAC devices that include one or more expandable elements that can expand and help to seal against the ostium. In some cases, the one or more expandable elements may be adapted to absorb or capture blood in order to expand. In some cases, the one or more expandable elements may include one or more coagulants such as but not limited to fibrinogen such that as the one or more expandable elements capture blood within the one or more expandable elements, the blood coagulates and thus helps to expand the one or more expandable elements into contact with the irregular ostium and to stay in that expanded configuration. It will be appreciated that the one or more expandable elements expanding is distinct from the expandable frame 110 expanding from a collapsed configuration for delivery to an expanded configuration for deployment.

FIG. 4 is a schematic view of an illustrative LAAC device 200 that includes an expandable frame 210. The LAAC device 200 may be considered as being similar to the LAAC device 100, but includes an expandable element 220. The expandable element 220 extends around a periphery 222 of the expandable frame 210. Since FIG. 4 is a schematic cross-sectional view, the expandable element 220 appears as a single element near a top (in the illustrated orientation) of the LAAC device 200 and as a single element near a bottom of the LAAC device 200. It will be appreciated that the expandable element 220 extends all the way around the periphery 222 of the expandable frame 210. The periphery 222 may be considered as extending around a circumference of the expandable frame 210, for example.

The expandable element 220 may be considered as being formed of a fabric or polymeric sheet or layer, and is adapted to allow blood to flow into an interior of the expandable element 220. In some cases, the expandable element 220 may be open at a proximal end 224 of the LAAC device 200 in order to capture blood that is flowing into the LAA 10 in a direction indicated by an arrow 226. In some cases, the expandable element 220 may be open at a distal end 228 of the LAAC device 200 in order to capture blood that is flowing out of the LAA 10 in a direction indicated by an arrow 230. In some cases, the expandable element 220 may be porous to blood, thereby allowing blood moving in either direction to enter an interior of the expandable element 220.

The expandable element 220 may include a coagulant such as but not limited to fibrinogen disposed within the expandable element 220 such that blood flowing into the interior of the expandable element 220 will be caused to coagulate. In some cases, the expandable element 220 may be filled with a material that swells in response to contact with water. For example, the expandable element 220 may be filled with a hydrogel. Since water is a primary component of blood, the expandable element 220 will swell subsequent to deployment, thereby helping to seal between the LAAC device 200 and the irregular ostium. In some cases, the expandable element 220 may include a shape memory foam that will expand once the LAAC device 200 has been implanted.

Figure 5:
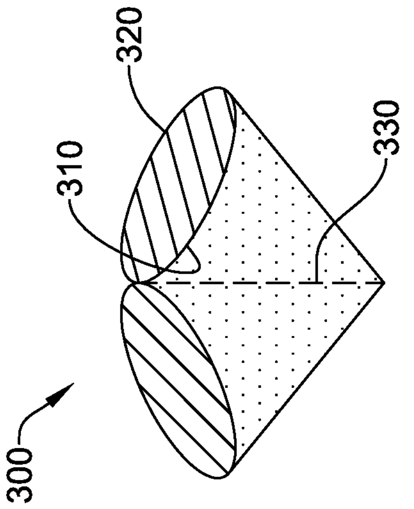
FIG. 5 is a schematic enlarged view of several filter bags.
Figure 7:
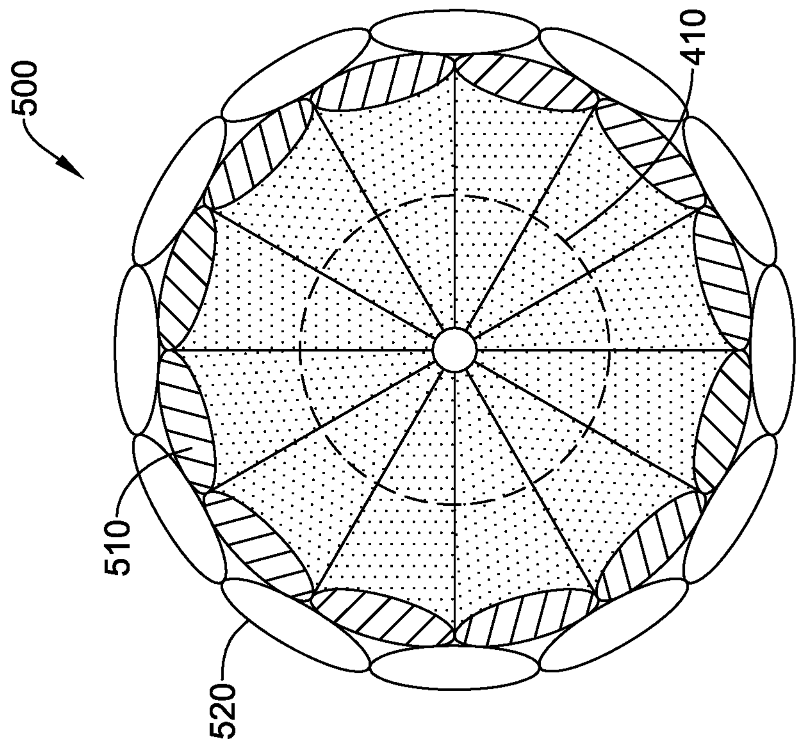
FIG. 7 is a schematic view of an expandable element that utilizes the filter bags of FIG. 5 and that may be combined with an LAAC device.
Figure 6:
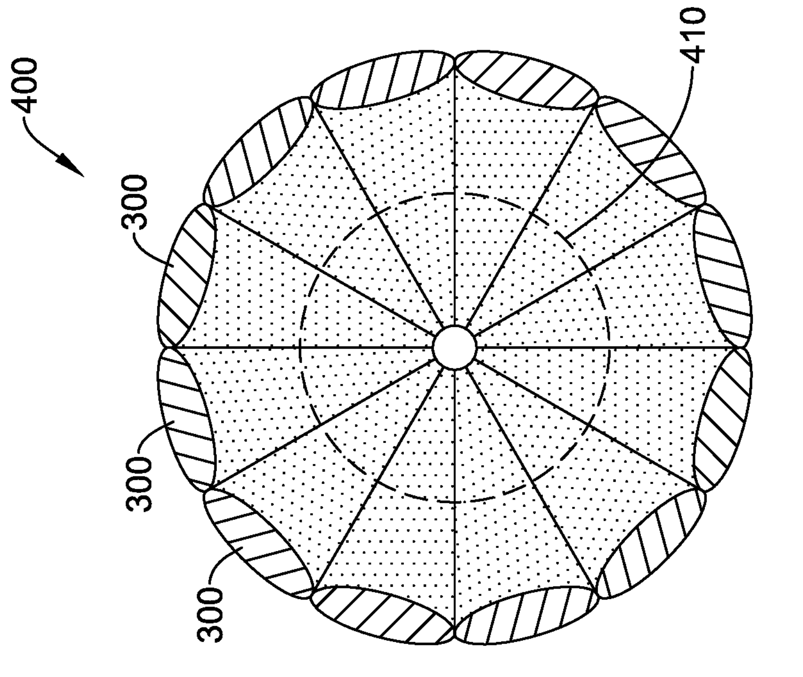
FIG. 6 is a schematic view of an expandable element that utilizes the filter bags of FIG. 5 and that may be combined with an LAAC device.

FIG. 5 is an enlarged schematic view of a two-layer bag filter 300 that may be used to form an expandable element. FIGS. 6 and 7 provide illustrative but non-limiting examples of expandable elements that may be formed using a number of the bag filters 300. In some cases, the two-layer bag filter 300 may include an inner layer 310 and an outer layer 320. The inner layer 310 and the outer layer 320 may be intermittently secured together via stitching 330 that forms conical structures as shown. In some cases, the bag filter 300 may be formed by forming conical shapes out of an appropriate material, and then securing adjacent conical shapes together adhesively or perhaps by stitching the adjacent conical shapes together.

The inner layer 310 and the outer layer 320 may be formed of any suitable materials, including materials that are blood-permeable. In some cases, the inner layer 310 and the outer layer 320 are formed of materials that are not blood-permeable. Examples of suitable materials for the inner layer 310 and the outer layer 320 include textiles or sheets or permeable sheets of PET (polyethylene terephthalate), polyesters, polyurethanes and fluoropolymers such as ePTFE (expanded polytetrafluoroethylene). In some cases, the bag filter 300 may include a coagulant that is coated on an interior of the bag filter 300. In some cases, the bag filter 300 may essentially be filled or at least partially filed with a coagulant.

As noted, the bag filters 300 may be combined together to form an expandable element that may subsequently be secured relative to an LAAC device such as the LAAC device 100 in order to form an LAAC device that better seals against an irregular ostium. FIG. 6 is a schematic view of an expandable element 400 that combines a plurality of bag filters 300. As shown in FIG. 5, the expandable element 400 may be formed by periodically stitching together an inner layer such as the inner layer 310 and an outer layer such as the outer layer 320. A dashed line 410 may be considered as representing the periphery of an LAAC device that the expandable element 400 may be secured to. Because the expandable element 400 is wider than the periphery of the LAAC device represented by the dashed line 410, it will be appreciated that the expandable element 400 may fold down over a periphery of the LAAC device, and thus may be positioned to seal between the LAAC device and an irregular ostium.

FIG. 7 is a schematic view of an expandable element 500 that may subsequently be secured relative to an LAAC device such as the LAAC device 100 in order to form an LAAC device that better seals against an irregular ostium. The expandable element 500 may be considered as including a first expandable element 510 and a second expandable element 520 that is disposed directly over the first expandable element 510. Each of the first expandable element 510 and the second expandable element 520 may be considered as being equivalent to the expandable element 400 shown in FIG. 6. Adding a second expandable element may provide additional sealing around the periphery of the LAAC device denoted by the dashed line 410. In some cases, the second expandable element 520 may be arranged such that the widened open portion of each filter bag within the second expandable element 520 fits between the widened open portions of each filter bag within the first expandable element 510.

Figure 8:
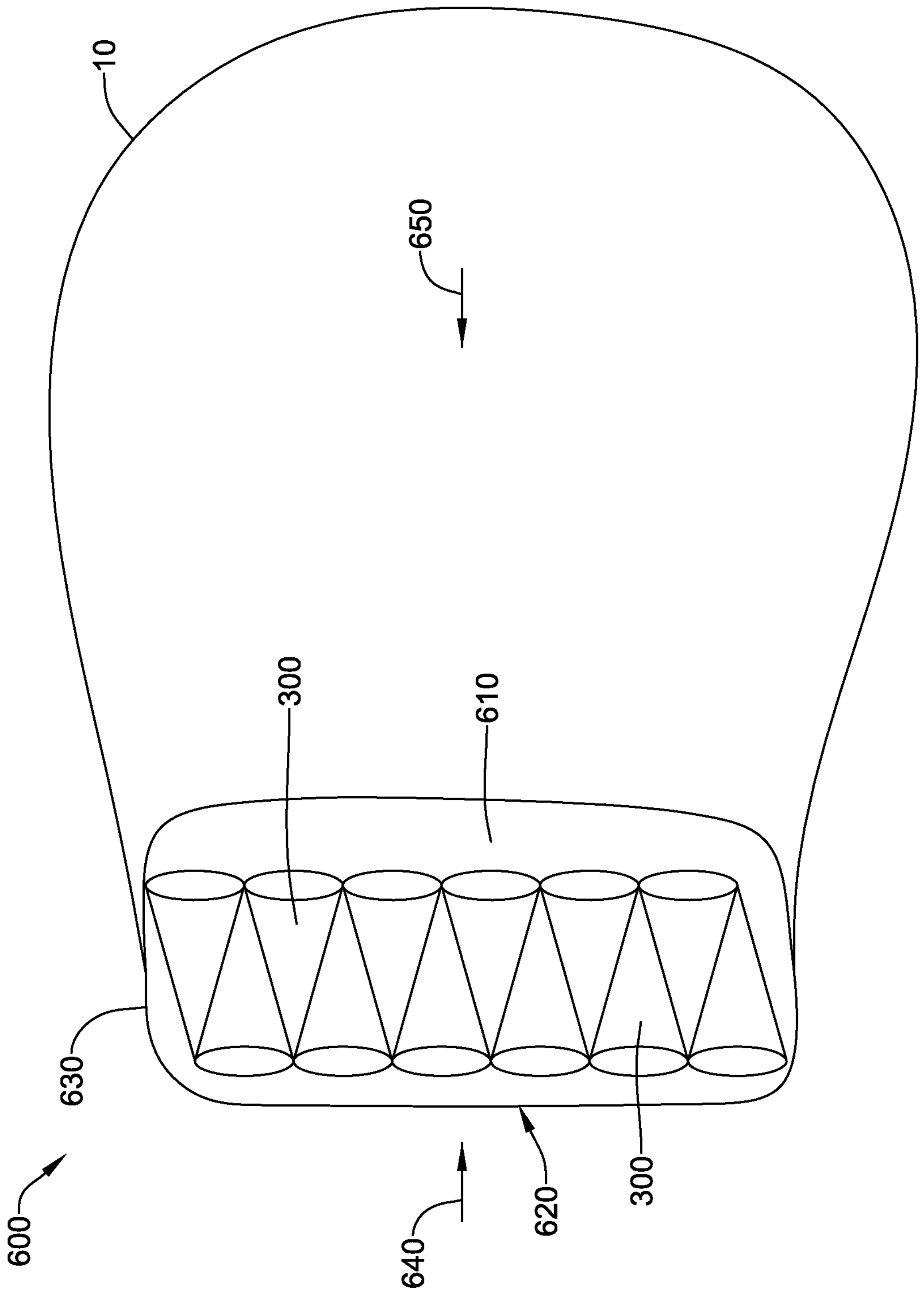
FIG. 8 is a schematic view of an illustrative LAAC device with an expandable element, the LAAC device shown disposed within an LAA.

FIG. 8 is a schematic view of an illustrative LAAC device 600 that includes an expandable frame 610. The expandable frame 610 may be considered as being similar if not identical to the expandable frame 110 described with respect to FIG. 2, and may or may not include a covering such as the covering 120. The LAAC device 600 includes an expandable element 620 that extends around a periphery 630 of the LAAC device 600. As can be seen, the expandable element 620 includes a number of bag filters 300, with some of the bag filters 300 positioned with an open end facing proximally in order to capture blood that is flowing towards or into the LAA 10 in a direction indicated by an arrow 640, and some of the bag filters 300 positioned with an open end facing distally in order to capture blood that is flowing away from or out of the LAA 10 in a direction indicated by an arrow 650. In some cases, the individual bag filters 300 may have a closed end. In some cases, the individual bag filters 300 may have two open ends, but may include a one-way valve that allows blood to flow through in a first direction but not in an opposing direction.

Figure 10:
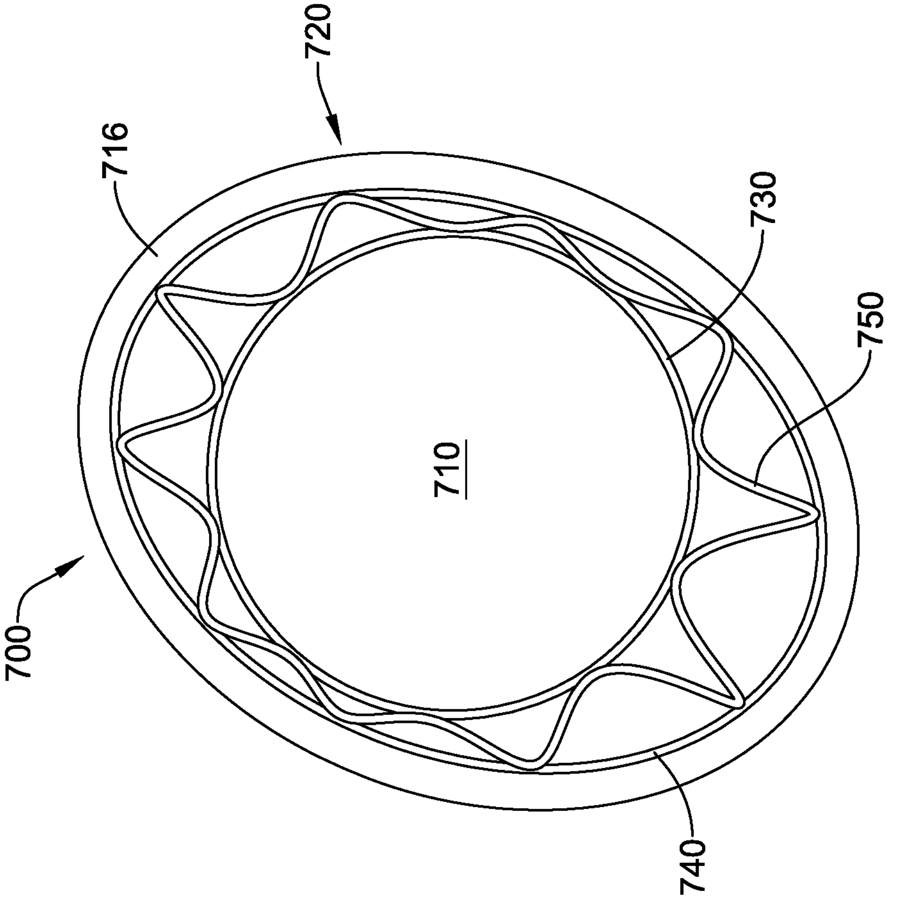
FIG. 10 is a schematic view of the illustrative LAAC device of FIG. 9 shown deployed within an irregular ostium.
Figure 9:
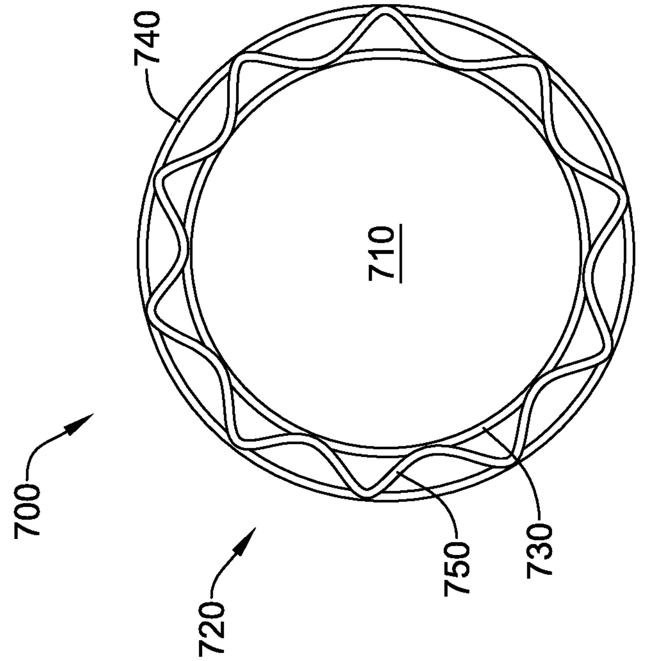
FIG. 9 is a schematic view of an illustrative LAAC device with a corrugated tri-layer expandable element.

FIG. 9 is a schematic view of an illustrative LAAC device 700 that includes an expandable frame 710. The expandable frame 710 may be considered as being similar if not identical to the expandable frame 110 described with respect to FIG. 2, and may or may not include a covering such as the covering 120. The LAAC device 700 includes a corrugated tri-layer expandable element 720. The corrugated tri-layer expandable element 720 may be adapted to swell in order to accommodate and seal against an irregular ostium 716, as shown in FIG. 10. The corrugated tri-layer expandable element 720 includes an inner layer 730 that fits against an outer surface of the expandable frame 710, an outer layer 740 that is adapted to seal against the irregular ostium 716, and an intermediate layer 750 that alternates between attachment or proximity to the inner layer 730 and attachment or proximity to the outer layer 740. In some cases, the intermediate layer 750 may be similar to that of the inner layer 730 and the outer layer 740. As an example, the architecture of the intermediate layer 750 may be similar to the alternating bags shown in FIG. 7. In some cases, swellable material may be secured or not secured to the intermediate layer 750. The swellable material may be secured to secured only to the inner layer 730, only secured to the outer layer 740 or in some cases may be secured to the inner layer 730, the outer layer 740 and the intermediate layer 750.

FIG. 10 shows the LAAC device 700 disposed within the irregular ostium 716. As can be seen, the corrugated tri-layer expandable element 720 has expanded or swelled to fill the space and thus seal against the irregular ostium 716. In some cases, the space between the inner layer 730 and the outer layer 740 fills with blood. In some cases, the space between the inner layer 730 and the outer layer 740 may include a coagulant that causes the blood entering the space to coagulate. In some cases, at least the outer layer 740 may be formed of a material that is permeable to blood, in order to allow blood to pass into the space between the inner layer 730 and the outer layer 740. Examples of suitable materials include textiles or sheets or permeable sheets of PET (polyethylene terephthalate), polyesters, polyurethanes and fluoropolymers such as ePTFE (expanded polytetrafluoroethylene).

Figure 11:
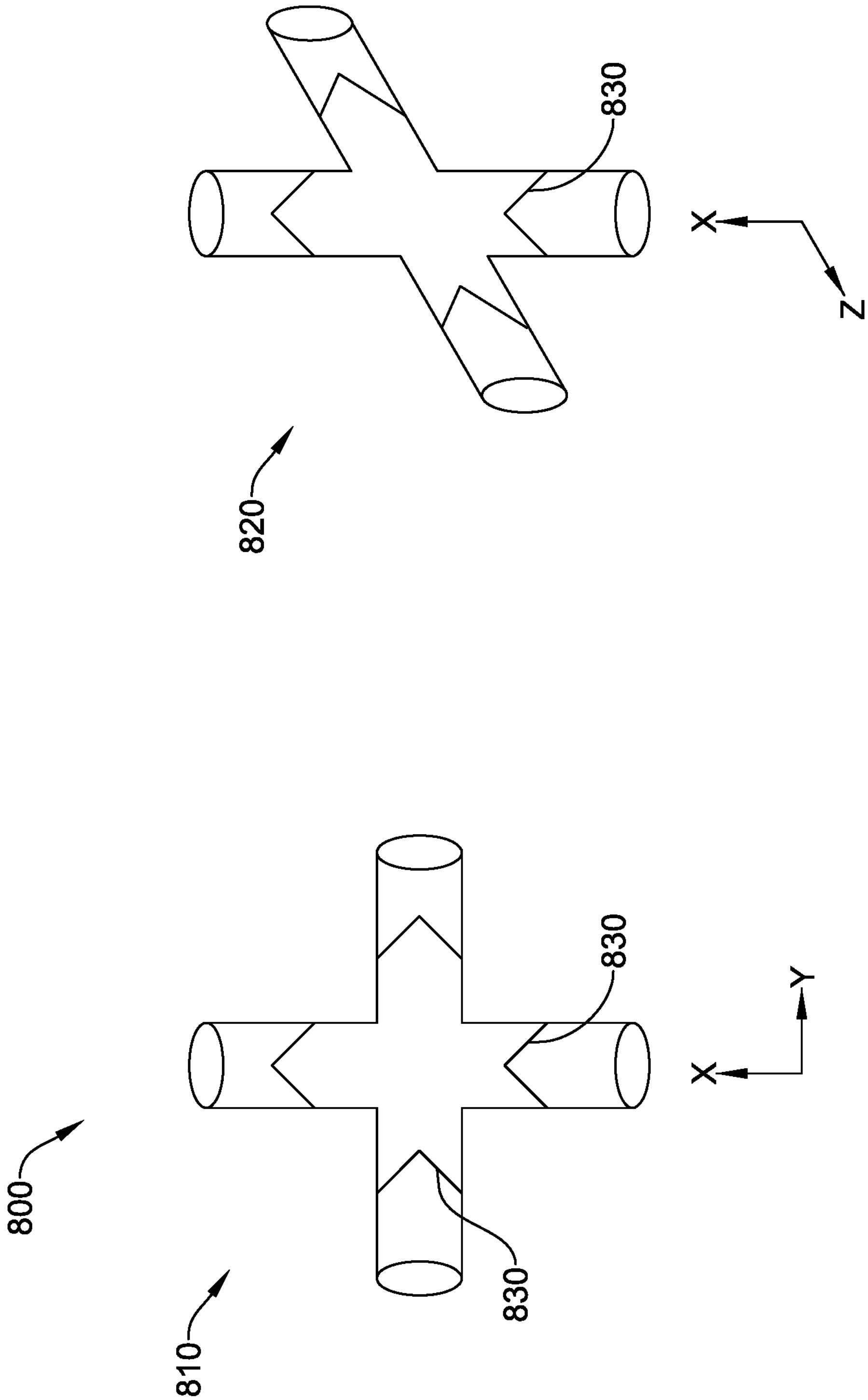
FIG. 11 is a schematic view of an illustrative valved mesh.

FIG. 11 is a schematic view of an illustrative valved mesh 800 that may be used as an expandable element with an LAAC device. As shown, the valved mesh 800 includes a first component 810 that is shown as being disposed within an XY plane and a second component 820 that is shown as being disposed within a YZ plane. It will be appreciated that this is merely illustrative, as the valved mesh 800 may not be laid out exactly within an XYZ coordinate system in which the components are arranged at right angles, but instead may take other angles between components. Each of the first component 810 and the second component 820 may be considered as including a number of one-way valves 830 that control in which direction(s) blood may flow through the valved mesh 800 and in which direction(s) blood is not allowed to flow through the valved mesh 800. In some cases, the valved mesh 800 may include a coagulant that causes blood that gets inside the valved mesh 800 to coagulate, thereby causing the valved mesh 800 to swell.

Figure 12A:
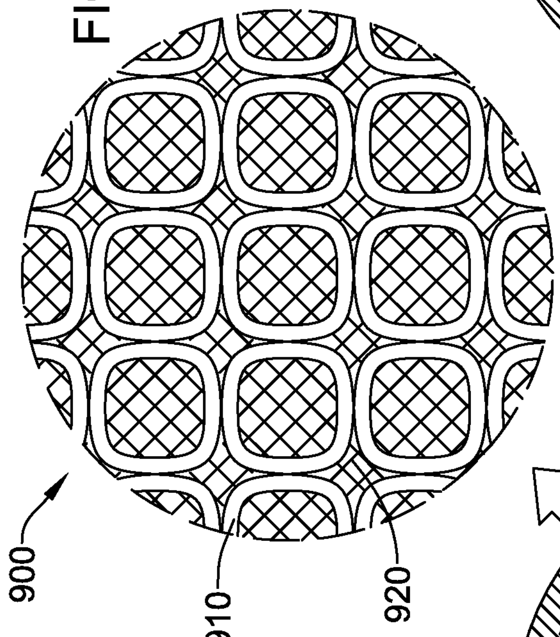
FIGS. 12A, 12B and 12C together provide views of an illustrative membrane material that may be used as a covering on the LAAC devices described herein.
Figure 12C:
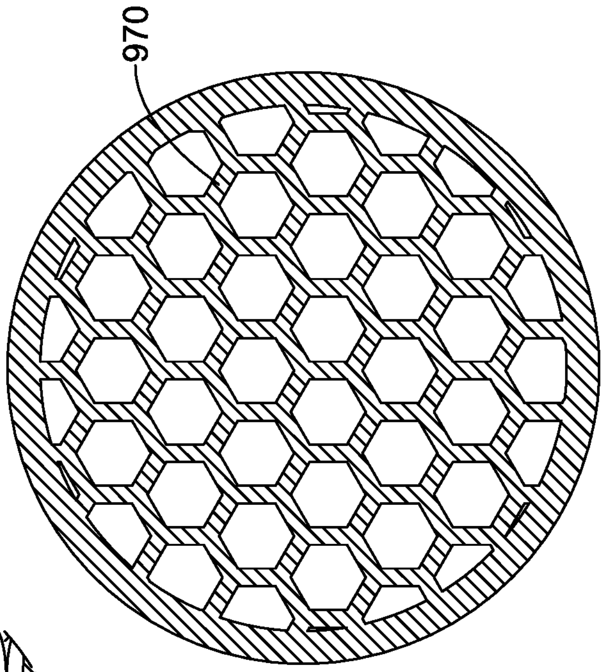
Figure 12B:
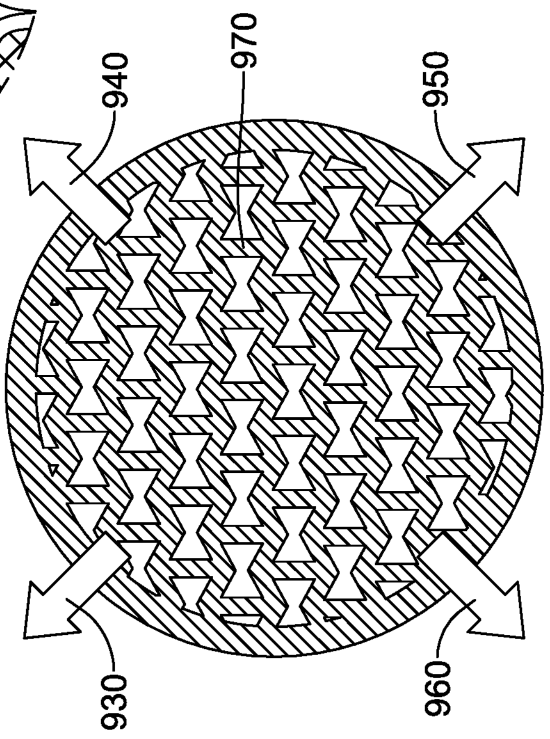

As will be appreciated, in some cases the covering (such as the occlusive element 120) that spans the expandable frame 110 may have to accommodate changes in the dimensions of the expandable frame 110. In other words, the covering may have to be able to stretch. FIGS. 12A, 12B and 12C together provide details of a covering 900 that may be used with the LAAC devices described herein. The covering 900 includes a webbing 910 that is made from a relatively thick fiber. A webbing 920 spans the distance between the relatively thick fibers forming the webbing 910 and is formed from relatively thin fibers. In some cases, the webbing 910 may be formed of fibers having an average diameter in a range of 5 to 10 μm and the webbing 920 may be formed of fibers having an average diameter in a range of 25 to 100 μm. In some cases, the webbing 910 is laid out in a honeycomb fashion, but this is not required in all cases.

In some cases, the webbing 910 may be formed of fibers that have a relatively large fraction of elastomer and a relatively smaller fraction of a second polymer such as but not limited to PET (polyethylene terephthalate). In some cases, the webbing 910 may be formed of fibers that are at least 50 percent elastomer and the webbing 920 may be formed of fibers that are at least 50 percent PET. In some cases, the webbing 910 may be formed of fibers that include about 70 percent elastomer and about 30 percent PET. In some cases, the webbing 920 may be formed of fibers that have a relatively large fraction of PET and a relatively smaller fraction of an elastomer. In some cases, the webbing 920 may be formed of fibers that include about 30 percent PET and about 70 percent elastomer. The elastomers used in the webbing 910 and the webbing 920 may include one or more of fluoroelastomers, polyurethane elastomers, PEBAX®, thermoplastic elastomers, copolyester elastomer, hydrophilic elastomers, polyamide 11 or polyether segments.

FIGS. 12B and 12C together illustrate how the covering 900 responds to applied forces. In particular, FIGS. 12B and 12C together show that tension applied in any direction, as indicated by the arrows 930, 940, 950 and 960, result in equal porosity. In FIG. 12C, the mesh 970 can be seen as having equal pore sizes. In some cases, the covering 900 may be considered as exhibiting auxetic properties. In some cases, the covering 900 may include materials such as urethane or nylon. In some cases, the covering 900 may also include radiopaque elements. In some cases, the covering 900 may be a fabric matrix that is formed in an auxetic pattern, such that stretching and compliance in a planar radial axis is equalized and distributed consistently regarding porosity of hemodynamic flow as well as hemostasis.

The devices described herein, as well as various components thereof, may be manufactured according to essentially any suitable manufacturing technique including molding, casting, mechanical working, and the like, or any other suitable technique. Furthermore, the various structures may include materials commonly associated with medical devices such as metals, metal alloys, polymers, metal-polymer composites, ceramics, combinations thereof, and the like, or any other suitable material. These materials may include transparent or translucent materials to aid in visualization during the procedure. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELC), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like.

In some embodiments, the system and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the system and/or other elements disclosed herein may include and/or be formed from a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun types. The type and denier of the yarn chosen may be selected in a manner which forms a biocompatible and implantable prosthesis and, more particularly, a vascular structure having desirable properties.

In some embodiments, the system and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethyl ketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed:

1. An implantable medical device, comprising:
- an expandable frame expandable between a collapsed configuration for delivery and an expanded configuration for deployment, the expandable frame including a periphery defined by the expandable frame;
- a covering spanning at least part of the expandable frame; and
- an expandable element secured relative to the periphery, the expandable element adapted to seal against an ostium of an LAA (left atrial appendage);
- wherein the expandable element comprises a plurality of bag filters that each have an open end and a closed end, and each of the plurality of bag filters are arranged around the periphery with the open end facing one direction and the closed end facing an opposing direction; and
- wherein at least some of the plurality of bag filters include a coagulant disposed within the bag filters.

2. The implantable medical device of claim 1, wherein each of the plurality of bag filters have an open end and a closed end, and each of the plurality of bag filters are arranged around the periphery in an alternating matter, with the open end of a bag filter arranged proximate a closed end of a neighboring bag filter.

3. The implantable medical device of claim 1, wherein the implantable medical device comprises an LAAC (left atrial appendage closure) device.

4. An LAAC (left atrial appendage closure) device adapted to fit within an irregular ostium of a patient's LAA (left atrial appendage), the LAAC device comprising:
- an expandable frame expandable between a collapsed configuration for delivery and an expanded configuration for deployment, the expandable frame including a periphery defined by the expandable frame, the expandable frame having a circular profile in the expanded configuration;
- a covering spanning at least part of the expandable frame; and three or more bag filters that are arranged around the periphery.

5. The LAAC device of claim 4, wherein each of the three or more bag filters have an open end and a closed end, and each of the plurality of bag filters are arranged around the periphery with the open end facing one direction and the closed end facing an opposing direction.

6. The LAAC device of claim 4, wherein each of the three or more bag filters have an open end and a closed end, and each of the three or more bag filters are arranged around the periphery in an alternating matter, with the open end of a bag filter arranged proximate a closed end of a neighboring bag filter.

7. The LAAC device of claim 4, wherein at least some of the three or more bag filters include a coagulant disposed within the bag filters.

* * * * *